(12) United States Patent
Cully et al.

(10) Patent No.: US 10,322,175 B2
(45) Date of Patent: Jun. 18, 2019

(54) CATHETER PACKAGE INCLUDING CATHETER STRAIGHTENING MEANS

(71) Applicant: W. L. Gore & Associates, Inc., Newark, DE (US)

(72) Inventors: Edward H. Cully, Flagstaff, AZ (US); James L. Goepfrich, Flagstaff, AZ (US); William G. Hardie, Flagstaff, AZ (US); Raymond P. Torrez, Surprise, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 0 days.

(21) Appl. No.: 15/522,577

(22) PCT Filed: Oct. 29, 2015

(86) PCT No.: PCT/US2015/058000
§ 371 (c)(1),
(2) Date: Apr. 27, 2017

(87) PCT Pub. No.: WO2016/069868
PCT Pub. Date: May 6, 2016

(65) Prior Publication Data
US 2017/0333668 A1 Nov. 23, 2017

Related U.S. Application Data

(60) Provisional application No. 62/073,710, filed on Oct. 31, 2014.

(51) Int. Cl.
*A61M 25/00* (2006.01)
*A61K 39/395* (2006.01)
(Continued)

(52) U.S. Cl.
CPC ........ *A61K 39/3955* (2013.01); *A61K 39/395* (2013.01); *A61K 39/39558* (2013.01);
(Continued)

(58) Field of Classification Search
CPC ....... A61B 1/00; A61B 1/00142; A61B 19/02; A61B 19/026; A61B 50/30; A61J 1/00;
(Continued)

(56) References Cited

U.S. PATENT DOCUMENTS 2,964,796 A 12/1960 Press
3,612,038 A 10/1971 Halligan
(Continued)

FOREIGN PATENT DOCUMENTS

EP 2106821 A1 10/2009
WO WO-2002015970 A1 2/2002

OTHER PUBLICATIONS

International Search Report and Written Opinion from PCT/US2015/058000, dated Jan. 25, 2016, 9 pages.

*Primary Examiner* — Bryon P Gehman (57) ABSTRACT

A catheter package and method of use which serve to straighten a curved catheter shaft. The straightening of the catheter shaft may be accomplished by passing the shaft through a pathway that bends the catheter in the opposite direction of the curvature imparted to the catheter shaft. The catheter shaft pathway may incorporate various shaped bumps, ridges, pins or rollers or other features which assist in straightening the shaft.

21 Claims, 9 Drawing Sheets

(51) Int. Cl.
*C07K 16/28* (2006.01)
*A61K 39/00* (2006.01)

(52) U.S. Cl.
CPC ...... *A61M 25/002* (2013.01); *A61M 25/0012* (2013.01); *A61M 25/0017* (2013.01); *C07K 16/2878* (2013.01); *A61K 2039/505* (2013.01); *A61K 2039/507* (2013.01); *A61K 2039/545* (2013.01); *A61M 25/0068* (2013.01); *C07K 2317/24* (2013.01); *C07K 2317/41* (2013.01); *C07K 2317/732* (2013.01); *C07K 2317/92* (2013.01)

(58) Field of Classification Search
CPC .... A61M 1/10; A61M 25/00; A61M 25/0012; A61M 25/0017; A61M 25/002; A61M 25/0068; A61K 39/395; A61K 39/3955; A61K 39/39558; A61K 2039/505; A61K 2039/507; A61K 2039/545; C07K 16/2878; C07K 2317/24; C07K 2317/41; C07K 2317/732; C07K 2317/92
USPC .......................................... 206/364, 365, 438
See application file for complete search history.

(56) References Cited

U.S. PATENT DOCUMENTS

| | | | | |
|---|---|---|---|---|
| 3,633,758 | A | * | 1/1972 | Morse ................. A61M 25/002 |
| | | | | 206/364 |
| 4,834,709 | A | | 5/1989 | Banning |
| 4,923,061 | A | | 5/1990 | Trombley |
| 5,105,942 | A | | 4/1992 | Van Veen |
| 5,607,055 | A | | 3/1997 | Bettinger |
| 5,848,691 | A | | 12/1998 | Morris |
| 5,947,284 | A | * | 9/1999 | Foster .................... A61B 50/30 |
| | | | | 206/364 |
| 6,024,764 | A | | 2/2000 | Schroeppel |
| 7,328,794 | B2 | * | 2/2008 | Lubs .................. A61M 25/002 |
| | | | | 206/364 |
| 9,744,333 | B2 | * | 8/2017 | Terzibashian ....... A61M 25/002 |
| 2005/0194276 | A1 | | 9/2005 | Lubs |
| 2005/0245847 | A1 | | 11/2005 | Schaeffer |
| 2008/0147013 | A1 | | 6/2008 | Breton |
| 2014/0110296 | A1 | | 4/2014 | Terzibashian |
| 2014/0262882 | A1 | | 9/2014 | Barnell |
| 2017/0340787 | A1 | * | 11/2017 | Corbett ............... A61M 25/002 |
| 2018/0021542 | A1 | * | 1/2018 | Terzibashian ....... A61M 25/002 |
| 2018/0177977 | A1 | * | 6/2018 | De Soto .................... B65B 5/02 |

* cited by examiner

CATHETER PACKAGE INCLUDING CATHETER STRAIGHTENING MEANS

CROSS-REFERENCE TO RELATED APPLICATION

This application is a national phase application of PCT Application No. PCT/US2015/058000, internationally filed Oct. 29, 2015, which claims the benefit of U.S. Provisional Application No. 62/073,710, filed Oct. 31, 2014, both of which are herein incorporated by reference in their entireties.

FIELD

The present disclosure relates to catheter packages and more particularly to a catheter packages and methods for straightening catheters.

BACKGROUND

Devices used in minimally invasive vascular procedures are commonly mounted upon catheters for remote access and delivery to the patient's circulatory system. Since the access site is purposely remote to the therapy or device delivery site, the catheter lengths can be quite long. There are several benefits to packaging and storing long catheters in a coiled configuration. A catheter packaged in a coil, rather than in a long straight length, will save space in manufacturing, in sterilization chambers, in transit and shipping, and on the shelf at the point of use. Smaller packaging will also reduce hospital waste.

Catheters and catheter packages are typically manufactured from biocompatible materials in the thermoplastic family. For purposes herein, the term "thermoplastic" refers to plastic materials that can repeatedly soften and become pliable above a certain temperature and return to a more solid state upon cooling. Thermoplastics tend to deform under stress and thus a catheter packaged in a coiled configuration will tend to take on the shape of the package over time and often acquire a bend bias having a bend radius. The resulting deformation may quicken in warmer environments such as those found in sterilization chambers and even during shelf life.

In a typical endovascular procedure, the initial entry site to the vascular system of a patient includes an introducer sheath and indwelling guide wire. The intended implant and its delivery catheter are mounted on the guide wire and traverse through the introducer. A stiff catheter shaft that is biased to a bend or having a bent configuration makes controlled insertion difficult at this point, thereby putting the patient at risk for inadvertent injury and trauma to the host vessel. Therefore, there is a need for devices, systems and methods for removing bend bias from catheters packaged in a bent configuration.

SUMMARY

The present disclosure generally relates to catheter packages, tools, and methods for removing a bend bias, or straightening, catheter shafts during or following removal from catheter packages.

In some embodiments, the straightening of the catheter shaft with a bend bias (i.e., one that tends to exhibit a curvature) is accomplished by passing the shaft through a pathway portion of the package that includes a reversal (a catheter straightening apparatus) that tends to bend the catheter in an opposite direction to that of the bend bias. The catheter shaft pathway may incorporate various reversal features such as bumps, ridges, pins, rollers, or tubular members, for example, which assist in bending the shaft against, or in an opposite direction of, the bend bias and the curvature of the catheter shaft. In some embodiments, the reversal features reduce friction produced during the bending process (e.g., in the case of free rotating rollers). In some embodiments, the catheter package includes a heat source to further aid in the increasing a bend radius, or straightening of a coiled or otherwise bent portion of a catheter shaft contained in the catheter package. In other embodiments, where a bend bias is desired in one or more portions of the catheter shaft (i.e., where it is desired that the catheter shaft take on a bend at the one or more portions), the catheter shaft pathway may be used to actually impart a curvature in a portion of a catheter shaft.

The phrase "substantial straightening of a curved portion of a catheter shaft" as used herein means that a curved portion of a packaged catheter shaft having a given bend radius will be straightened at least to the extent that the bend radius or radius of curvature is at least doubled by passing the curved portion through the reversal or straightening apparatus of the catheter package. The phrase "at least partial straightening of a curved portion of a catheter shaft" as used herein means that a curved portion of a packaged catheter shaft having a given bend radius will be straightened at least to the extent that the bend radius or radius of curvature is increased at least ten percent by passing the curved portion through the reversal or straightening apparatus of the catheter package.

The present disclosure includes an apparatus for straightening a catheter shaft, the apparatus comprising a catheter package shaped to contain a catheter shaft wherein at least a portion of the catheter shaft is curved or bent in a first direction to define a first bend radius; and a catheter shaft pathway physically associated with the catheter package, the catheter shaft pathway including at least one reversal configured to bend the catheter shaft in a second direction opposite to the first direction as the catheter shaft is passed through the catheter shaft pathway. The present disclosure includes a catheter package comprising: a catheter having a catheter shaft that is biased with a bend having a bend radius; a catheter package configured to retain a catheter shaft in a curved configuration; and a straightener slidably receiving the catheter shaft and including at least one reversal configured to increase the bend radius as the catheter shaft is slid through the straightener.

The instant disclosure also includes a method of straightening a catheter shaft contained in a catheter package comprising selecting a catheter package containing a catheter with a catheter shaft that has been biased with a curvature to define a curved portion having a bend radius, the catheter package including a straightening apparatus; and drawing the curved portion of the catheter shaft through the straightening apparatus to increase the bend radius.

While various features and advantages are summarized above, additional features and advantages are also contemplated in the instant disclosure.

BRIEF DESCRIPTION OF THE DRAWINGS

The accompanying drawings are included to provide a further understanding of the disclosure and are incorporated in and constitute a part of this specification, illustrate embodiments, and together with the description serve to explain various principles of the disclosure.

DETAILED DESCRIPTION

Persons skilled in the art will readily appreciate that various aspects of the present disclosure can be realized by any number of methods and apparatuses configured to perform the intended functions. It should also be noted that the accompanying drawing figures referred to herein are not necessarily drawn to scale, but may be exaggerated to illustrate various aspects of the present disclosure, and in that regard, the drawing figures should not be construed as limiting.

Figure 1:
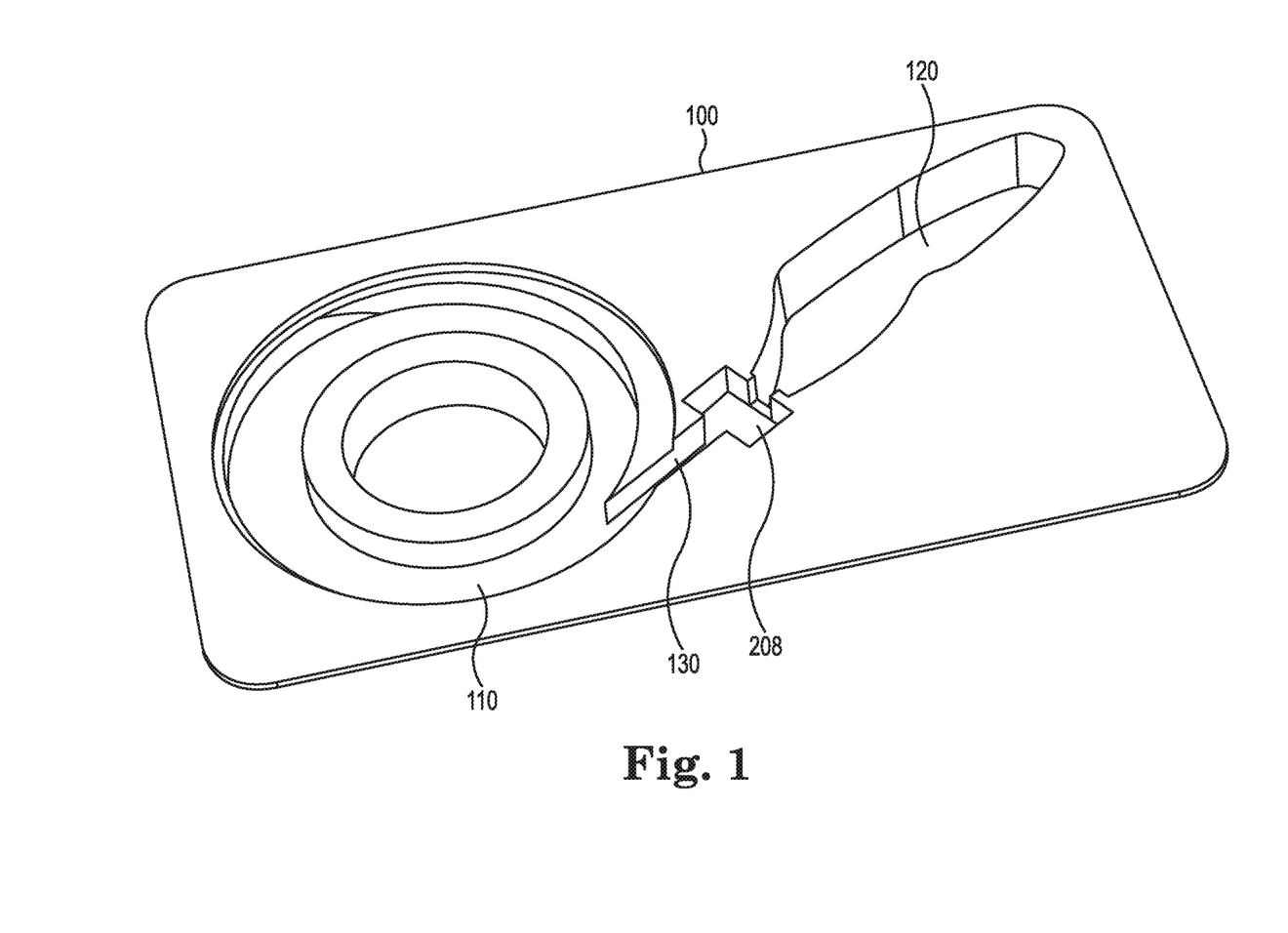
FIG. 1 depicts a perspective view of an endovascular device package (e.g., a catheter package) that includes a straightening apparatus.

FIG. 1 shows a package 100, according to some embodiments. A catheter may be placed within this package 100 with portions of the package 100 shaped to hold, or contain the catheter. For example, the majority of the catheter length may be stored in a coiled configuration within a catheter holder 110. In some embodiments, the catheter hub or handle is placed within the package 100 in an adjoining depression 120.

As indicated in FIG. 1, a portion of the package 100 contains a groove 130, from which the catheter shaft exits the catheter holder 110 and connects with the depression 120. In this region, a space 208 for accommodating a straightening apparatus (such as straightening apparatus 200 shown in FIGS. 1A-1C) is incorporated into the package 100. During removal of the catheter, the technician, clinician, or other user will remove the hub or handle from the depression 120 and begin to pull the catheter from the package 100. Tension applied will cause the catheter shaft to unwind within the catheter holder 110 and pass through a straightening apparatus placed within space 208.

Figure 1A:
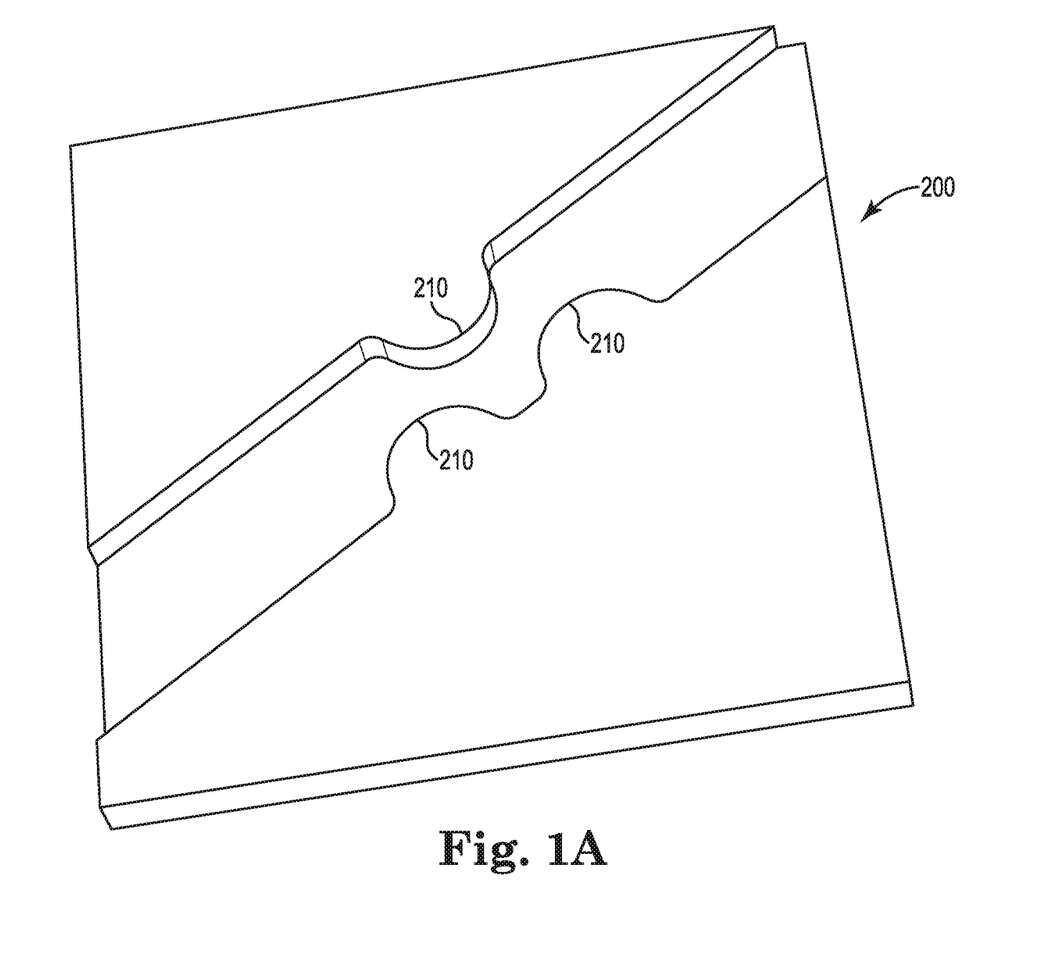
FIG. 1A depicts a close-up of formed protrusions utilized within the straightening apparatus.

As seen in more detail in FIG. 1A, the straightening apparatus 200 may comprise a series of protrusions 210, posts, nubs, or reversals, which cause the catheter to deform as it passes through them. Herein, the term "reversal" is meant to describe a means for the application of opposing forces to opposite sides of the previously coiled catheter shaft, which either entirely or partially removes the bias from the catheter shaft to a curved or coiled configuration. In other words, drawing a portion of the catheter shaft through the reversal entirely or partially defeats the previously bent or coiled configuration of that portion of the catheter shaft. The size, shape and placement of these protrusions 210 is matched to the size of the catheter outside diameter, the coil radius, and the catheter material, for example. Although fixed positions are generally indicated for the protrusions 210, it is contemplated that adjustable positions, adjustable sizes (e.g., replacement with different diameter protrusions), and combinations thereof are also applicable as desired. By applying tension to the catheter, the catheter is drawn through the straightening apparatus 200, where the bias to a bend, or bent shape, is defeated.

Although the terms "coil," "coiled," "curved," "curled," "bend," or "bent" are used throughout this document in describing the catheter shafts and the manner in which they are packaged, it should be understood that any configuration that reduces the footprint of the package is within the scope of the disclosure. For example, a length of catheter shaft that has been folded back and bent 180 degrees would result in an undesired curvature imparted to the catheter shaft (i.e., the catheter shaft would be biased to naturally take on a bent shape) that could benefit from being straightened by straightening apparatus 200. As such, the terms "coil," "coiled," "curved," "curled," "bend," and "bent" should be broadly read to include any manipulation of a catheter shaft to allow it to be packaged within a package of shorter length than the overall maximum length of the catheter. The terms "coil," "coiled" "curled," "bend," and "bent" include, but are not limited to, configurations wherein the catheter is curved through a bend of at least about 270 degrees, as well as more than one complete 360 degree curve. Helically curved configurations are also considered to be coils.

Figure 1B:
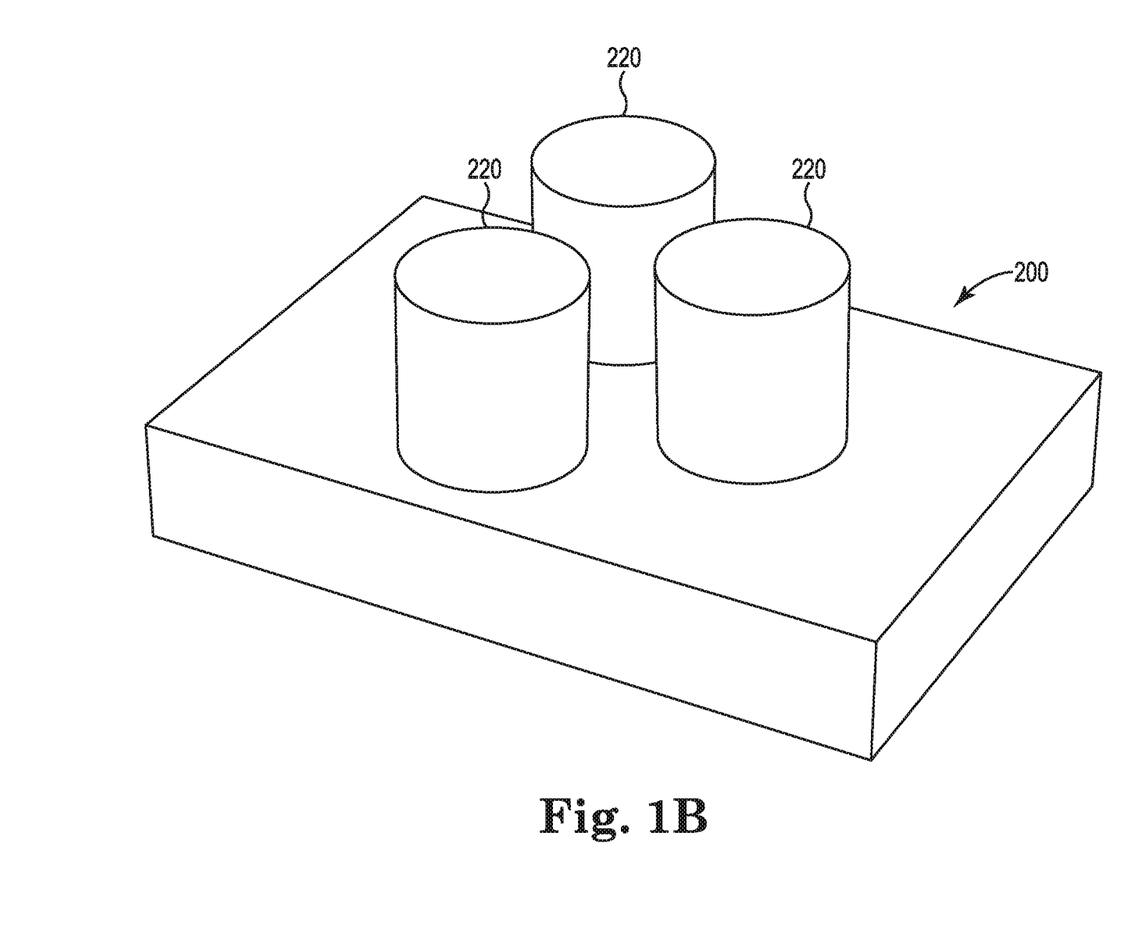
FIG. 1B depicts a close-up of a series of pins utilized within the straightening apparatus.
Figure 1C:
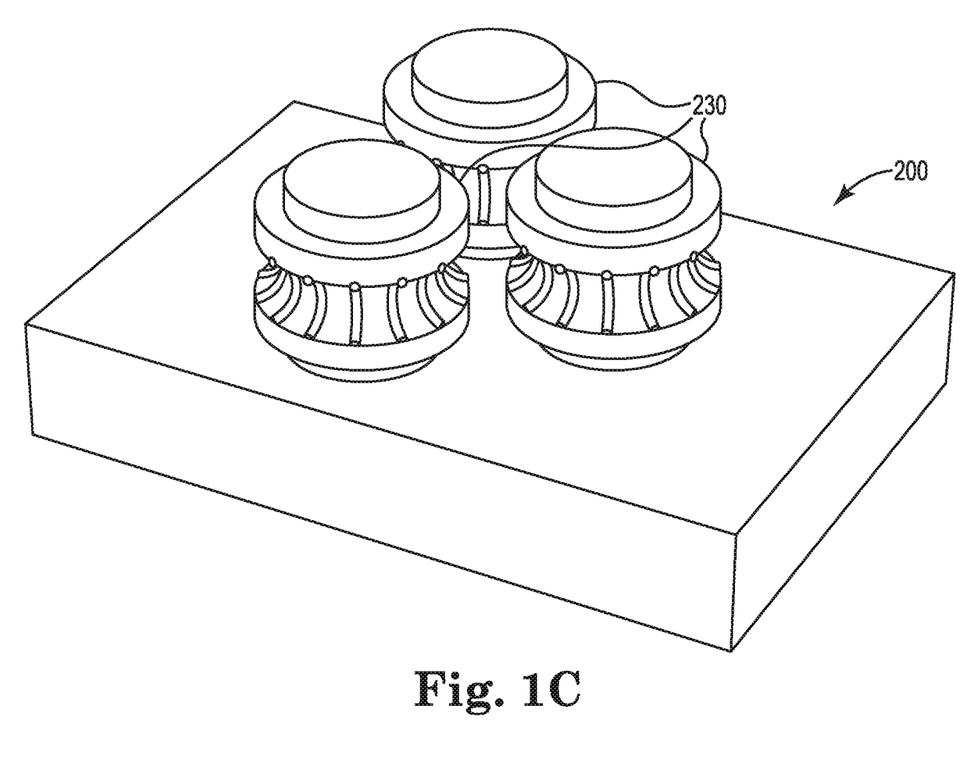
FIG. 1C depicts a close-up of a series of rollers utilized within the straightening apparatus.
Figure 1D:
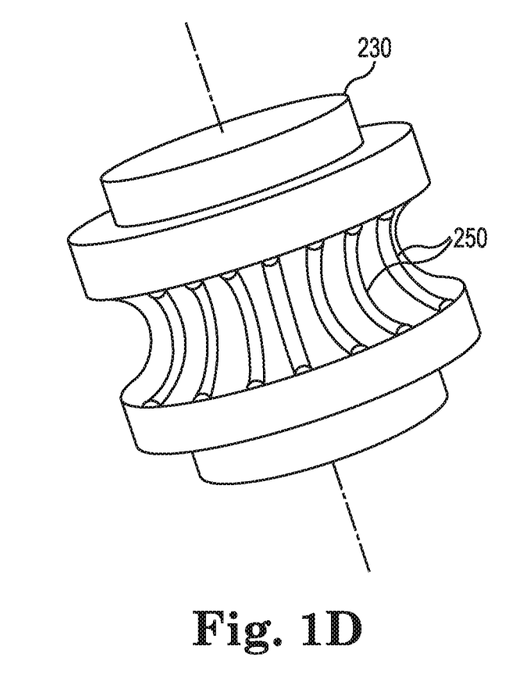
FIG. 1D depicts a close up of a textured roller.

FIG. 1B depicts the reversals as fixed pins 220. As described previously, fixed pins 220 have similar function as the formed protrusions 210 of FIG. 1A. FIG. 1C depicts the reversals in the form of rollers 230 that are able to rotate about an axis. The roller 230 diameters are designed in order that they may affect the pathway of the catheter. In some embodiments, when the catheter shaft is passed by the rollers 230, the bent bias is at least partially defeated and the catheter emerges in a relatively straight configuration. As shown in FIG. 1D, the rollers 230 may have a smooth finish or may contain a texture 250 in such a way as to assist in stretching or shrinking the catheter material. Stretching material along the inner radius (intrados) or compressing material along the outer radius (extrados), or performing both stretching and compressing simultaneously on opposing sides of the catheter shaft, will assist in defeating the previous bias with a bend or coil configuration of the catheter shaft.

It is also apparent that combinations of pins, protrusions and rollers may be used together. For example, a pair of pins may be used on one side of the catheter shaft with a single opposing roller on the opposite side of the catheter shaft. Additionally, it is contemplated that the package may include a selection of reversal features (e.g., bushings of various diameters or rollers of various diameters) selected by the user to achieve a desired increase in a bend radius or reduction in curvature such as increase a radius of curvature. It should also be understood that, should the user desire to do so, only portions of the catheter shaft may be straightened, or one or more portions of the catheter shaft may alternatively be caused to have a greater bias toward a curved configuration, as desired. For example, the catheter shaft can be rotated 180 degrees and drawn through the reversal features to impart a curvature, or bend bias, to the catheter shaft as desired.

The reversal or straightening apparatus 200 may be modular, meaning it may be placed into the catheter package 100 as a modular component, which may also be removed from the catheter package 100. This enables straightening apparatus 200 of various dimensions suitable for different catheter shaft diameters to be utilized in a single catheter package 100. The straightening apparatus 200 may also be provided directly as a portion of the catheter package 100, such that the straightening apparatus 200 is not removable from the package 100 (e.g., where the catheter package 100 and straightening apparatus 200 are molded as a single, integral unit). Moreover, straightening apparatus 200 is optionally formed as a combination of integral and modular components with the package 100.

It is envisioned that the reversals can be dimensioned and located to facilitate passing the catheter shaft through the straightening apparatus 200. Other catheter components such as hubs, handles, or other features normally will not be passed through the straightening apparatus 200. As another example, implantable devices carried by the catheter (usually mounted at the end opposite the hub or handle) normally will not be passed through the straightening apparatus 200. Ensuring that the catheter and endoprosthesis remain undamaged can be accomplished by mounting the straightening apparatus 200 in a break-away fashion. The straightening apparatus 200 may tolerate a certain amount of force (enough to straighten the catheter shaft). At a higher force, the pathway may be designed to pop open in order to prevent risk of damage to an implantable device or to catheter components. Typically this "higher force" is selected to be significantly lower than any force needed to damage the catheter, catheter components, attachment bonds of various components, or the endoprosthesis itself.

In some cases, catheter shafts may be placed in a spiral coil tube (e.g., a flat spiral with constantly changing radius or a helix), or in an elongated oval package. Catheters packaged as such will require varying amounts of straightening and, as such, a variable version of the straightening apparatus 200 is envisioned. The reversals within the catheter pathway may be configured to adjust as needed to provide the correct amount of straightening force for varied regions of the catheter length. In some instances, it may be desirable for portions of the catheter shaft to bypass the straightening apparatus 200 altogether. In these instances, the catheter shaft may be elevated up and out of the catheter pathway, or a bypass pathway that does not contain reversals may be incorporated into the package.

Figure 2A:
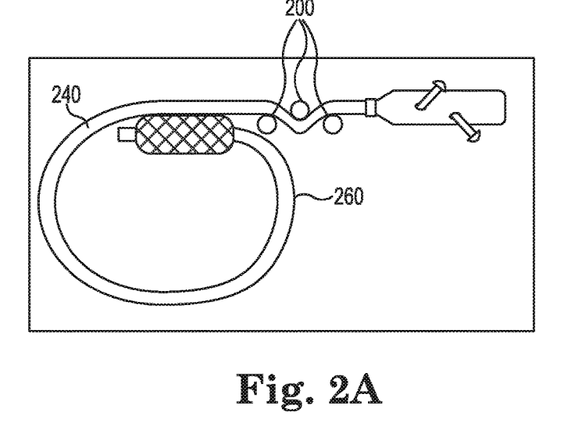
FIG. 2A depicts a plan view of a coiled catheter in a package
Figure 2B:
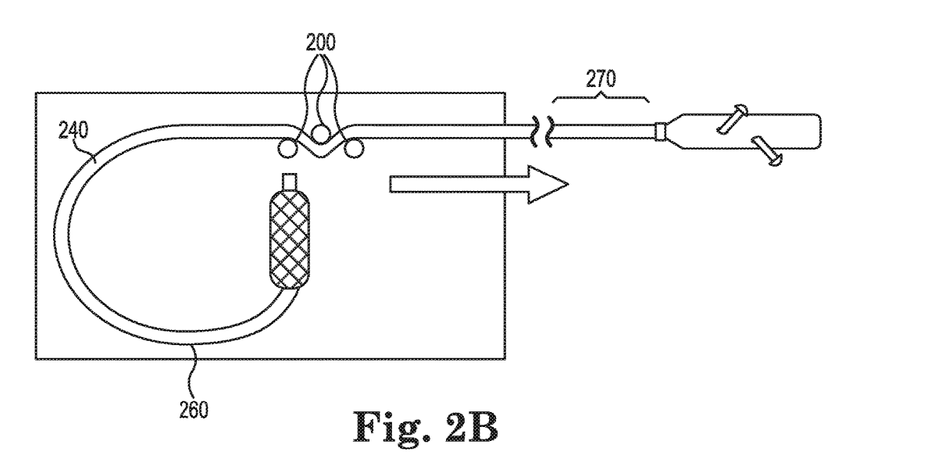
FIG. 2B depicts a plan view of a catheter being withdrawn from a package
Figure 2C:
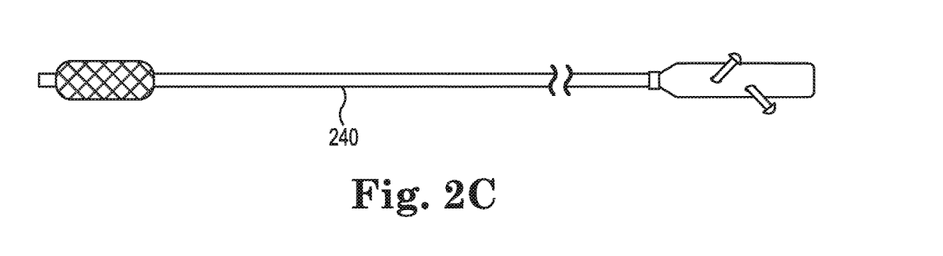
FIG. 2C depicts a plan view of a catheter having been removed from a package.

FIG. 2A depicts a catheter shaft 240 in a packaged configuration with at least a portion of the catheter shaft 240 curved and defining a bend radius 260. Catheter shaft 240 is held in a curved configuration by the package. Over time, the catheter shaft 240 may take on the shape, and thus be biased to naturally exhibit the bend radius 260 in which the catheter shaft 240 is constrained. In order to present a straightened catheter to an implanting clinician or other user, the package is equipped with a straightening apparatus 200. As depicted in FIG. 2B, when catheter shaft 240 is passed through straightening apparatus 200, the bend bias of the catheter shaft 240 having a bend radius 260 is at least partially defeated, resulting in an at least partially straightened region 270. Once the entire catheter shaft 240 is passed through straightening apparatus 200, the bend bias of the catheter shaft 240 is removed and the catheter shaft 240 is substantially straightened, as depicted in FIG. 2C, allowing for a more controlled insertion into the patient's anatomy.

Figure 3:
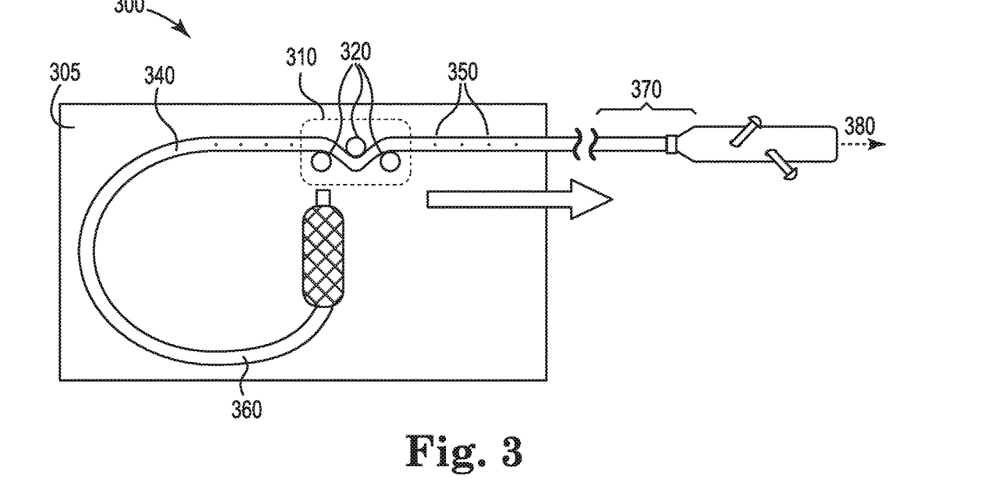
FIG. 3 contains a schematic view of a catheter package containing a straightening apparatus.

FIG. 3 illustrates certain features of a catheter package 300, according to some embodiments. The catheter package 300 generally comprises a catheter holder 305 within which a catheter may be packaged. In general, the catheter package 300 contains a catheter holder 305 and a straightening apparatus 320, the catheter holder 305 configured to receive a catheter shaft 340 packaged in a curled configuration having a portion 360 with a bend radius. The straightening apparatus 320 generally contains at least one reversal that bends the catheter shaft 340 in an opposite direction than the direction in which the catheter is curled in the catheter package 300. In use, the catheter shaft 340 enters the straightening apparatus 320 and emerges from the straightening apparatus 320 with the bend bias defeated forming an at least partially straightened region 370. As shown, the catheter shaft 340 is advanced through the straightening apparatus 320 by sliding the catheter shaft 340 in the direction indicated by arrow 380. By advancing the catheter through the straightening apparatus 320 in the direction of travel, the length of the catheter shaft 340 is bent though a radius (e.g., an acute angle) to reduce or remove any imparted curvature or bend bias in the catheter shaft 340.

As shown in FIG. 3, a catheter package 300 may include a straightening apparatus 320 (indicated generally by box 310), that is integrally formed with the catheter holder 305. The straightening apparatus 320 can be formed from the same material as the catheter holder 305 (e.g., the entire catheter package 300 may be formed as one piece). For example, the catheter package 300 may be injection molded as a catheter holder 305 with posts, protrusions, nubs, or reversals molded as one piece to form the catheter package 300. In some embodiments, the posts, protrusions, nubs, or reversals that formed with catheter holder 305 comprise the entire straightening apparatus 320.

In some embodiments, the catheter package 300 only has certain elements of the straightening apparatus 320 integrally formed with the catheter holder 305. For example, the catheter holder 305 may be integrally formed with one or more posts or poles that form axles around which one or more rollers (e.g., such as roller 230 in FIG. 1D) are rotatably received.

In some embodiments, during formation of the catheter package 300, the catheter holder 305 is configured to contain a catheter shaft 340 that is curved, wound, coiled, or otherwise bent in a first plane. As a part of packaging, at least a portion of the catheter shaft 340 is often wound in a single plane around a central axis, although helical or other configurations are contemplated. In some embodiments, the straightening apparatus 320 is oriented to bend the catheter shaft 340 about a radius (e.g., to form an acute angle) in the same plane as that in which the catheter shaft 340 is curved. Similar to prior embodiments, the straightening apparatus 320 optionally includes pins, rollers, or combinations thereof that have central axes oriented parallel to the central axis about which the catheter shaft 340 is wound.

As shown, the catheter package 300 is configured such that the catheter shaft is received in the proper orientation to remove the bend bias. Additional or alternative means for proper orientation include providing markers 350, guides, or tracks on the catheter shaft 340, catheter package 300, or both to help guide the catheter shaft 340 through the straightening apparatus 320 in a desired orientation. For example, markers 350 are optionally used to help users or assemblers of the package to maintain proper orientation of the catheter shaft 340 relative to the straightening apparatus 320. Thus, various embodiments include a method of use in which the markers 350 are employed to ensure that the straightening apparatus 320 bends the catheter shaft 340 in an opposite direction to that of the bend bias.

Figure 4:
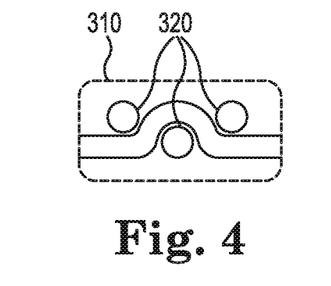
FIG. 4 is a schematic view of a removable straightening apparatus according to some embodiments.

In an alternative embodiment, the catheter holder 305 can be formed without a straightening apparatus 320 integrally formed with the catheter holder 305. The straightening apparatus 320 can be formed separately from the catheter holder 305 and later joined, or otherwise physically associated with the catheter holder 305 to form a complete catheter package 300. As shown in FIG. 4, the straightening apparatus 320 can be formed as a standalone component, with the components within box 310 later added or secured to the catheter holder 305 to form a catheter package 300 having a straightening apparatus 320. Any of the components illustrated in FIG. 1B, 1C, or 1D, for example, can be formed separately from the catheter holder 305.

Figure 5:
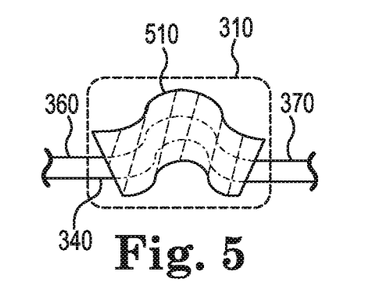
FIG. 5 is a schematic view of a straightening apparatus according to some embodiments.

FIG. 5 shows another straightening apparatus in the form of a tubular member 510 that is shaped to receive a catheter shaft 340 that can be drawn within the tubular member 510 to straighten the catheter shaft 340. The tubular member 510 defines an internal tubular path, or channel, that generally includes at least two directional changes or reversals to bend the catheter shaft 340 as it is drawn through the tubular member 510.

As described in association with other embodiments, the catheter shaft 340 has a portion 360 with a bend bias defining a bend radius. During straightening, the portion 360 enters the tubular member 510 and exits the tubular member 510 at least partially straightened by the tubular member 510 to define a straightened region 370. Thus, a straightening operation, or a reversal operation, is accomplished as desired using the tubular member 510, where the catheter shaft 340 is drawn through the tubular member 510 through the internal, tubular path of the tubular member 510, to impart a desired bend to a portion of the catheter shaft 340 to remove a bend bias from the catheter shaft 340. In other embodiments, the catheter shaft 340 is optionally rotated 180 degrees and drawn through the tubular member 510 to actually impart a bend bias to the catheter shaft 340, although it is contemplated that the tubular member 510 would generally be used to remove or reduce a bend bias.

In some embodiments, the tubular member 510 is formed as a single pieced of tubing material, although separate, connected pieces are contemplated. For example, the tubular member 510 is optionally formed from multiple components, such as two halves that are able to be assembled together. In some embodiments, the tubular member 510 has a clamshell configuration with a first concave half and a second concave half that are capable of being coupled together. For example, the first and second halves may be joined by a hinge on a first side and a clamp or clasp on a second side to close the first and second halves together. In use, the first and second halves may be joined by a hinge on a first side, such that the catheter shaft 340 is placed within the first and second halves and the first and second halves are hingedly closed around the catheter shaft 340 to form the tubular member 510. Although a hinge and clasp arrangement is described, any variety of assembly methods (e.g., snap-fit, fasteners, or adhesives) are contemplated.

The tubular member 510 can be preassem bled to a catheter shaft 340 prior to packaging; can be attached to catheter shaft 340 after removal from the package (e.g., formed in a clamshell configuration with two separate parts attached together over the catheter shaft); or a first portion can be formed as a part of a catheter holder (e.g., catheter holder 305) with a second portion later assembled the first portion (e.g., half the clamshell could be integrally formed with the catheter holder.

Where the tubular member 510 is formed separately from a catheter holder 305, the tubular member 510 may be assembled to the catheter holder 305 to be physically associated with the catheter holder 305 to form the catheter package 300. For example, a catheter holder 305 is optionally formed with a complementary pocket (not shown) for receiving the tubular member 510. In another embodiment, the tubular member 510 is formed as a removable unit that is attachable to the catheter holder 305. The removable unit contains the components that make up the tubular member 510 and can be added to the catheter holder 305.

Figure 6:
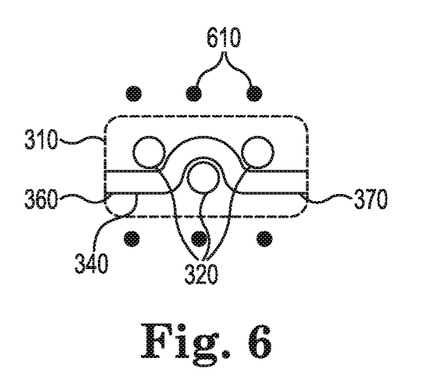
FIG. 6 is a schematic view of a straightening apparatus with heating elements according to some embodiments.

In some embodiments, the catheter shaft is fabricated from thermoplastic material such that the application of heat at the site of straightening can help soften the catheter shaft material and assist in the straightening process. For example, it is contemplated that heating could help reduce the force required for straightening and/or the amount of over-bending required to achieve a desired reduction in curve bias in the catheter shaft. Various manners of introducing heat during straightening are contemplated. For example, a heater such as an electrical heating element 610 having electrical wires or heating coils such as those shown in FIG. 6 can be included. The heating elements 610 (e.g., heating coils) are connected to a power source (not shown) such as an electrical outlet or battery. The heating elements 610 are arranged about the straightening region to delivery heat to the catheter shaft 340 as it moves through the straightening region.

Other means for heating that could be incorporated into the package include chemical heating elements or chemical reactants (e.g., chemicals in a pouch or bag) situated close to the straightening region or use of exothermic reactions (e.g., via phase change materials). Examples of devices capable of providing exothermic material phase changes include pouches with super saturated solutions of sodium acetate. By initiating crystallization at a nucleation site, such pouches can provide sufficient heat to enhance the straightening process without requiring an additional "warming" step from the clinician or their staff. Other possible heating mechanisms include warming the catheter shaft 340 or even the entire package using a heating pad, IV warming bag, bowl of warm water or an oven.

In still other embodiments, heat is applied via mechanical means. For example, heat is optionally applied to the catheter by inducing friction in rollers similar to those of previously described embodiments. The rollers and the posts on which they rotate may be configured to generate friction between them as the rollers rotate, according to some embodiments. The friction would heat the rollers and thus the catheter shaft as it passes over the rollers. Means for inducing friction between the rollers and the shafts could include surface roughening or other features for generating friction between the rollers and the shafts about which they rotate.

Figure 7:
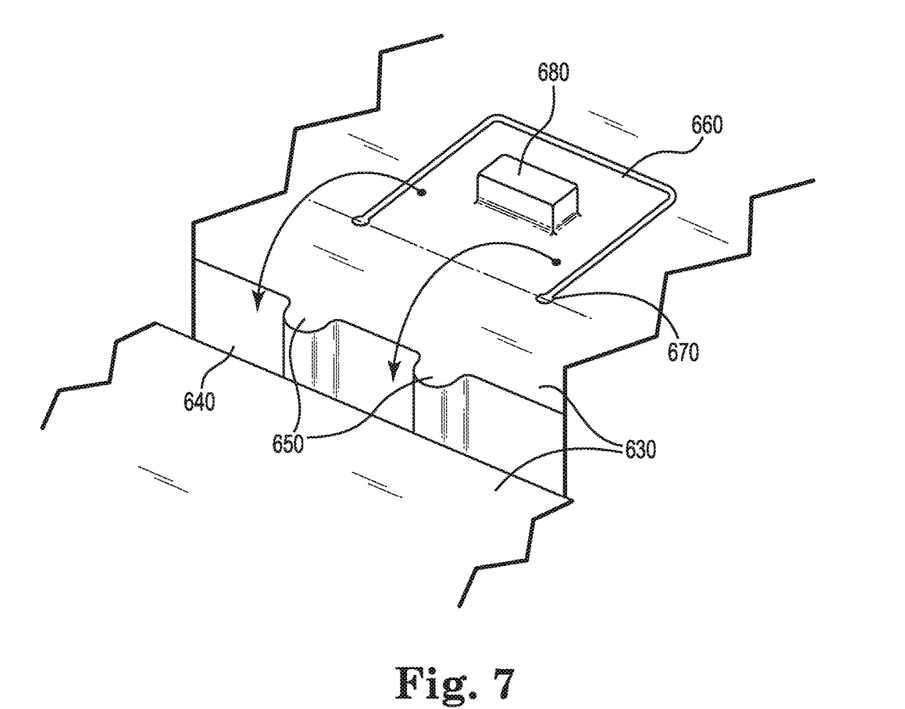
FIG. 7 is a schematic view of a removable straightening apparatus according to some embodiments.

In some embodiments, the catheter package contains a partially removable reversal attached to the catheter package. For example, as illustrated in FIG. 7, a hinged or foldable flap 660 is attached to the catheter package and the flap 660 may contain a portion of the reversal. A surface 630 of the catheter package is shown on both sides of a groove 640 in the catheter package. The groove 640 is sized to receive a catheter shaft (not shown). The groove 640 includes at least one nub or protrusion 650 extending from the catheter package into the groove 640. The hinged or foldable flap 660 is attached to the surface 630 of the catheter package and folds over the surface 630 of the catheter package. The flap 660 contains a projection 680 such as a pin, bump, knob, or cylinder. The projection 680 is sized and shaped to fit within the groove 640 between the protrusions 650 with a space remaining between the projection 680 and the protrusions 650 that is large enough for the catheter shaft to slide within. The flap 660 is attached to the catheter shaft surface with a hinge 670 or folded region allowing the flap 660 to fold over and lie adjacent to the catheter surface 630.

In some embodiments, a catheter with a bend bias is placed within the groove 640. The flap 660 is then closed with the projection 680 located in the groove 640 on one side of the catheter shaft with the protrusions 650 positioned on the opposite side. The catheter shaft is then passed between the projection 680 and the protrusions 650 as the catheter shaft is slid through the groove. In some embodiments, the projection 680 and the protrusions 650 are sized and shaped to provide at least one reversal in order to guide the catheter shaft through at least one acute angle bend in order to remove the bend bias in the catheter shaft. The flap 660 may be opened or closed depending on a user's needs. For example, the flap 660 may be first opened to accommodate devices attached to the catheter shaft that have a greater diameter than the catheter shaft. At any point in the process, for example, after most of the catheter shaft is slid through the groove 640, a user may open the flap 660 to remove the catheter shaft from the groove 640. In at least this manner, a user is able to easily disengage the reversal and/or remove the catheter shaft from the reversal before devices on the end of the catheter reach the reversal.

It should also be understood that, while various embodiments are described in association with catheter shafts and associated packaging, the present disclosure is also applicable to any variety medical tubing and associated packaging, such as filaments, cannula, intravenous lines, and other rubber or plastic hosing.

Numerous characteristics and advantages of the present disclosure have been set forth in the preceding description, including preferred and alternate embodiments together with details of the structure and function of the disclosure. The disclosure is intended as illustrative only and as such is not intended to be exhaustive. It will be evident to those skilled in the art that various modifications may be made, especially in matters of structure, materials, elements, components, shape, size and arrangement of parts within the principals of the disclosure, to the full extent indicated by the broad, general meaning of the terms in which the appended claims are expressed. To the extent that these various modifications do not depart from the spirit and scope of the appended claims, they are intended to be encompassed therein.

What is claimed is:

1. An apparatus for straightening a catheter shaft, the apparatus comprising:
    a catheter package shaped to contain a catheter shaft wherein at least a portion of the catheter shaft is curved in a first direction to define a first bend radius; and
    a catheter shaft pathway physically associated with the catheter package, the catheter shaft pathway including at least one reversal feature, comprising a plurality of rollers, configured to bend the catheter shaft in a second direction opposite to the first direction as the catheter shaft is passed through the catheter shaft pathway.

2. The apparatus of claim 1, wherein the catheter shaft pathway is integrally formed with the catheter package.

3. The apparatus of claim 1, wherein the at least one reversal feature is removable from the catheter package.

4. The apparatus of claim 1, wherein the at least one reversal feature comprises protrusions.

5. The apparatus of claim 1, wherein the at least one reversal feature comprises a tubular member configured to receive the catheter shaft.

6. The apparatus of claim 1, further comprising a heater configured to heat the catheter shaft as it passes through the catheter shaft pathway.

7. The apparatus of claim 6, wherein the heater comprises an electrical heating element.

8. The apparatus of claim 6, wherein the heater comprises a chemical heating element.

9. The apparatus of claim 1, wherein the catheter shaft pathway is configured to bend the catheter shaft through an acute angle.

10. The apparatus of claim 1, further comprising a catheter including a catheter shaft received in the catheter package, the catheter shaft having a bias to a radius of curvature and the catheter shaft pathway being configured to at least double the radius of curvature upon passing the catheter shaft through the catheter shaft pathway.

11. A catheter package comprising:
    a catheter having a catheter shaft that is biased with a bend having a bend radius;
    a catheter package configured to retain a catheter shaft in a curved configuration; and
    a straightener including a heater configured to heat the catheter shaft and the straightener slidably receives the catheter shaft and includes at least one reversal feature configured to increase the bend radius as the catheter shaft is slid through the straightener.

12. The catheter package of claim 11 wherein the straightener is attached to the catheter package.

13. The catheter package of claim 11 wherein the straightener includes a modular component that is removable from the catheter package.

14. The catheter package of claim 11 wherein the at least one reversal feature comprises protrusions.

15. The catheter package of claim 11 wherein the at least one reversal feature comprises a plurality of rollers.

16. The catheter package of claim 11 wherein the heater includes an electrical heating element.

17. The catheter package of claim 11 wherein the heater includes an exotherm is heating device.

18. The catheter package of claim 11 wherein the straightener is configured to increase the bend radius of the catheter shaft by at least ten percent as the catheter shaft passes through the straightener.

19. The catheter package of claim 11 wherein the catheter package is sized to receive the catheter shaft in a coiled configuration.

20. A method of straightening a catheter shaft contained in a catheter package comprising:
    selecting a catheter package containing a catheter with a catheter shaft that has been biased with a curvature to define a curved portion having a bend radius, the catheter package including a straightening apparatus and the straightening apparatus includes at least one of a heater configured to heat the catheter shaft and a plurality of rollers; and
    drawing the curved portion of the catheter shaft through the straightening apparatus to increase the bend radius.

21. The method of claim 20 wherein drawing the catheter shaft through the straightening apparatus increases the bend radius by at least ten percent.

* * * * *